United States Patent
Marczuk

(10) Patent No.: US 11,628,019 B2
(45) Date of Patent: Apr. 18, 2023

(54) METHOD FOR GENERATING A REFERENCE INFORMATION ITEM OF AN EYE, MORE PARTICULARLY AN OPTICALLY DISPLAYED REFERENCE RHEXIS, AND OPHTHALMIC SURGICAL APPARATUS

(71) Applicant: Carl Zeiss Meditec AG, Jena (DE)

(72) Inventor: Piotr Marczuk, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 758 days.

(21) Appl. No.: 16/582,836

(22) Filed: Sep. 25, 2019

(65) Prior Publication Data

US 2020/0100851 A1 Apr. 2, 2020

(30) Foreign Application Priority Data

Sep. 28, 2018 (DE) .......................... 102018124065.1

(51) Int. Cl.
| | |
|---|---|
| *A61B 34/00* | (2016.01) |
| *A61F 9/007* | (2006.01) |
| *A61B 90/00* | (2016.01) |
| *A61B 90/20* | (2016.01) |
| *A61B 3/14* | (2006.01) |
| *A61B 17/00* | (2006.01) |
| *A61B 34/20* | (2016.01) |

(52) U.S. Cl.
CPC ................ *A61B 34/25* (2016.02); *A61B 3/14* (2013.01); *A61B 90/20* (2016.02); *A61F 9/00754* (2013.01); *A61B 2017/00119* (2013.01); *A61B 2017/00973* (2013.01); *A61B 2034/2065* (2016.02); *A61B 2034/252* (2016.02); *A61B 2090/373* (2016.02)

(58) Field of Classification Search
CPC ........ A61B 3/14; A61B 90/20; A61F 9/00754
See application file for complete search history.

(56) References Cited

U.S. PATENT DOCUMENTS

| | | | |
|---|---|---|---|
| 2004/0102799 A1 | 5/2004 | Perez et al. | |
| 2011/0019150 A1 | 1/2011 | Schuhrke et al. | |
| 2014/0243623 A1* | 8/2014 | Kersting | ............. A61B 3/1005 600/301 |
| 2018/0098812 A1* | 4/2018 | Ootsuki | ................. A61B 34/20 |

FOREIGN PATENT DOCUMENTS

DE 102009053208 A1 8/2011

* cited by examiner

*Primary Examiner* — Jason M Ip
(74) *Attorney, Agent, or Firm* — Walter Ottesen, P.A.

(57) ABSTRACT

An aspect of the disclosure relates to a method for generating a reference information item of an eye, wherein at least one characterization information item that characterizes a rhexis size and/or a rhexis position of a potential actual rhexis on an anterior capsular bag wall of the eye is input into an input unit of an ophthalmic surgical apparatus and, depending on the characterization information item, a reference rhexis is determined as at least a constituent part of the reference information item of the eye by an evaluation unit of the ophthalmic surgical apparatus, wherein the determined reference rhexis is optically displayed by an optical display unit of the ophthalmic surgical apparatus. The disclosure further relates to an ophthalmic surgical apparatus.

12 Claims, 2 Drawing Sheets

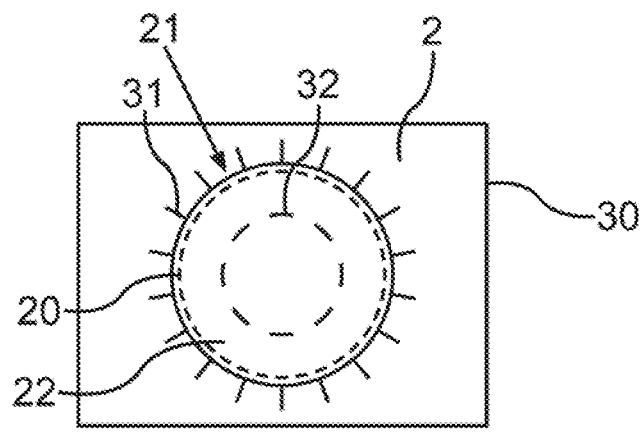
Fig.2
FIG. 3A
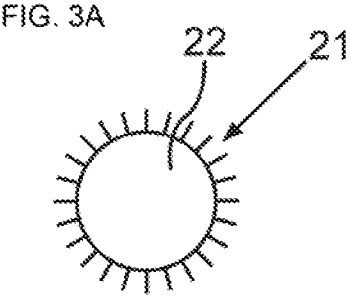
FIG. 3B
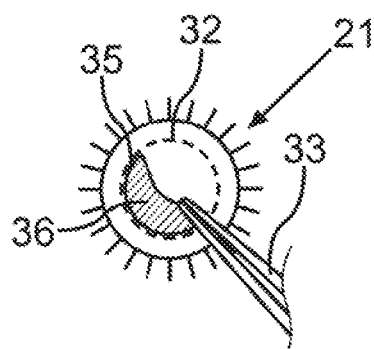
FIG. 3C
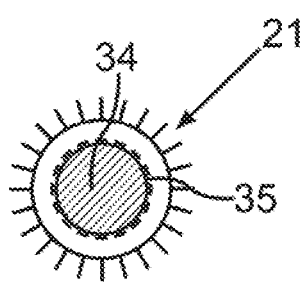
FIG. 3D
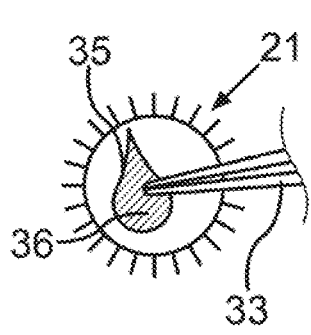
FIG. 3E
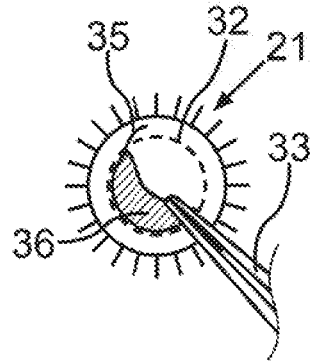

METHOD FOR GENERATING A REFERENCE INFORMATION ITEM OF AN EYE, MORE PARTICULARLY AN OPTICALLY DISPLAYED REFERENCE RHEXIS, AND OPHTHALMIC SURGICAL APPARATUS

CROSS REFERENCE TO RELATED APPLICATION

This application claims priority of German patent application no. 10 2018 124 065.1, filed Sep. 28, 2018, the entire content of which is incorporated herein by reference.

FIELD OF THE INVENTION

One aspect of the invention relates to a method for producing a reference information item of an eye. A further aspect of the invention relates to an ophthalmic surgical apparatus.

BACKGROUND OF THE INVENTION

In the case of ophthalmic surgical interventions on the eye, for example when removing a natural lens from the eye and replacing this natural lens with an implanted intraocular lens, this natural lens is removed from the capsular bag of the eye. To this end, it is necessary to open the capsular bag. In this context, producing an opening on an anterior capsular bag wall for the purposes of removing the natural lens is known.

In this context, opening the capsular bag at its anterior capsular bag wall, for example by the action of laser radiation, and thereby producing a hole in this anterior capsular bag wall is known.

In contrast to such procedures, mechanical tearing tools such as needles or forceps, for example, are known. These tools are introduced through an incision in the cornea, produced in advance by means of a surgical knife, and the anterior capsular bag wall is lacerated by these mechanical tearing tools by way of the direct action on the anterior capsular bag wall. This also produces an appropriate opening in the anterior capsular bag wall in order to then be able to remove the natural lens from the capsular bag. By way of example, the natural lens can be removed by phacoemulsification.

In comparison with non-mechanical tearing tools, as are exemplified by lasers, for example, these mechanical tearing tools are widespread, particularly for reasons of costs.

However, inaccuracies when forming the tear are possible in the case of these mechanical tearing tools. This may arise by virtue of an inaccurate rhexis arising on the anterior capsular bag wall on account of the handling of the mechanical tearing tool by the surgeon. This may result in inaccurate and unwanted directions of the rhexis and/or undesirably large or undesirably narrow forms of the openings on the anterior capsular bag wall. If such disadvantages occur and rhexis sections occur, which extend up to the peripheral edge of the forward capsule bag wall, then a disadvantage can thereby result, that the intraocular lens to be subsequently implanted can no longer be reliably and securely held in the capsular bag. It may even be the case in individual cases (typically ~1%) that the anterior capsular bag lacerates so far that it is no longer possible at all to fasten an intraocular lens therein and thereby additional surgical complexity and a higher risk of further complications arise. Even though these disadvantages arise in the case of mechanical tearing tools, these tools are very widespread in medical interventions on account of low costs and a relatively fast production of an opening in the anterior capsular bag wall.

SUMMARY OF THE INVENTION

It is an object of the invention to provide a method and an ophthalmic surgical apparatus which can be used to provide a reference information item of an eye in order, in particular, to be able to carry out a rhexis on the capsular bag in more accurate and reliable fashion using a mechanical tearing tool.

This object can, for example, be achieved by a method for generating a reference information item of an eye. The method includes: inputting at least one characterization information item characterizing at least one of a rhexis size and a rhexis position of a potential actual rhexis on an anterior capsular bag wall of the eye into an input unit of an ophthalmic surgical apparatus; determining, in dependence upon the characterization information item, a reference rhexis as at least a constituent part of the reference information item of the eye via an evaluation unit of the ophthalmic surgical apparatus; and, optically displaying the determined reference rhexis via an optical display unit of the ophthalmic surgical apparatus.

The object can, for example, further be achieved by an ophthalmic surgical apparatus having: an input unit configured for inputting at least one characterization information item characterizing at least one of a rhexis size and a rhexis position of a potential actual rhexis on an anterior capsular bag wall of the eye; an evaluation unit configured to determine, in dependence upon the characterization information item, a reference rhexis as at least a constituent part of the reference information item of the eye; and, an optical display configured to display the determined reference rhexis via an optical display unit of the ophthalmic surgical apparatus.

An aspect of the invention relates to a method for generating a reference information item of an eye. In particular, this reference information item can be used in the case of a surgical intervention on the eye. By way of example, a surgical intervention can be assisted by this reference information item and the surgical intervention on the eye can be implemented in an improved fashion, more particularly more accurately, as a result thereof.

In the method, at least one characterization information item is input into an input unit of an ophthalmic surgical apparatus. As a result of the characterization information item, a rhexis size and/or a rhexis position of a potential and desired actual rhexis on an anterior capsular bag wall of the eye are/is characterized. Depending on the characterization information item, a fictitious reference rhexis is determined as at least one constituent part of the reference information item of the eye by an evaluation unit of the ophthalmic surgical apparatus. The reference rhexis can be the reference information item. A further information item that forms the reference information item together with the reference rhexis may also be available in addition to the reference rhexis. The determined reference rhexis is optically displayed by an optical display unit of the ophthalmic surgical apparatus. An information item about an advantageous rhexis, as should be produced on an anterior capsular bag wall during a surgical intervention on the eye, for example, is determined by the ophthalmic surgical apparatus by way of such a method. Therefore, a theoretical reference rhexis is initially determined, independently of an actual surgical intervention to be subsequently performed. In particular, the reference rhexis is determined for an individual eye such that even an eye-individual determination of the reference rhexis by the ophthalmic surgical apparatus is facilitated. Consequently, the best-possible and desired reference rhexis is determined for the surgeon in advance, independently of an actual surgical intervention, and this reference rhexis then still is also optically displayed in particularly advantageous fashion. As a result, the surgeon can also visually perceive the determined reference rhexis and can themselves assess the latter. Moreover, this optical display of the determined theoretical reference rhexis also improves the mental perception of a surgeon.

By virtue of a rhexis size and/or rhexis position being counted as a characterization information item, in particular by medical staff, in particular by the surgeon, it is already possible to predetermine essential initial variables. A reference rhexis that is particularly suitable for reality and consequently suitable for use, for example, in a real surgical intervention or else in a surgical intervention that is practiced by simulation for the specific eye can be produced, particularly by way of such a characterization information item.

Consequently, the method also renders it possible to optically provide a reference information item, specifically the reference rhexis. As a result, it can be used in needs-based fashion in a surgical intervention. This also means that it can then be made available to a surgeon as an information item during specific phases of a surgical intervention. This can also be used in parallel during the surgical intervention for the purposes of monitoring the surgical intervention. As a result, the surgical result is improved or it is possible to correct a surgical intervention, even still during the intervention. However, even already independently of the actual surgical intervention, this production and provision of the reference rhexis is particularly advantageous to the effect of this reference rhexis being available prior to a surgical intervention and the surgeon already being able to identify independently of the real surgical intervention and, in particular, even before the real surgical intervention whether this reference rhexis is also suitable and, where applicable, whether it meets the requirements for the eye to be operated. Moreover, the method can also be used, for example, on dummy eyes for test situations or simulations or for training purposes, for example for improving the training of specialist medical staff. In particular, the method consequently also renders it possible to learn how an actual rhexis can be performed on an anterior capsular bag wall without performing an actual real surgical intervention so as also to be able to produce a particularly accurate, desired and needs-based opening in the anterior capsular bag wall, even if such a mechanical tearing tool is used.

In this context, as also already indicated above, the optical representation of this reference rhexis substantially contributes to an improved understanding of the position and/or size of a rhexis and consequently, in the context of the individual eye for which this reference rhexis then is provided, facilitates an improved visual understanding of where this reference rhexis may then be situated and how it could in fact be formed in the anterior capsular bag wall. In particular, the reference rhexis is presented in the spectral range that is visible to humans.

In particular, the reference rhexis is an optical aiding element, in particular an aiding line, for a surgical intervention on the capsular bag. In particular, the reference rhexis is an optically displayed surgical auxiliary information item, in particular an optically displayed surgical aiding line, more particularly, a surgical aiding line along which an actual rhexis should be implemented in the anterior capsular bag wall for the purposes of producing a hole as an opening in the anterior capsular bag wall.

The reference rhexis represents the region that should preferably be lacerated on the anterior capsular bag wall. The actual rhexis is the region on the anterior capsular bag wall that is lacerated. Here, a tear or tear line, which forms the boundary of the actual rhexis, is produced in the anterior capsular bag wall.

In an embodiment, provision is made for the reference rhexis to be optically displayed in an eyepiece of a surgical microscope of the ophthalmic surgical apparatus. By way of example, this surgical microscope can be a pair of spectacles that the surgeon may wear. This can be a particularly advantageous embodiment since the optically displayed reference rhexis consequently always is in the visual field of the surgeon.

In addition or as an alternative thereto, provision can be made for the reference rhexis to be optically displayed on a screen of the ophthalmic surgical apparatus. This screen can be separate from a surgical microscope.

Advantageously, a rhexis line, more particularly continuous rhexis line, can be determined and optically displayed as a reference rhexis. A rhexis line may be a non-closed line and, for example, may be at least one line segment or line section of a closed line, for example a circular line. Preferably, this rhexis line can be a circular line. Consequently, as a result of this embodiment, precisely that path along which the anterior capsular bag wall should be lacerated in order to produce the opening in the anterior capsular bag wall is optically determined and displayed.

A line prevents a relatively large area from being optically displayed and, for example, completely covering other regions. Only a line being presented in this context also avoids other information items to be displayed by the display unit not being restricted or undesirably covered by an areal representation of the reference rhexis. Therefore, a rhexis line is a particularly advantageous embodiment of an optically displayed reference information item.

In an embodiment, in which a rhexis line is determined and optically displayed as a reference information item, provision can be made for this rhexis line to be immediately presented completely and in the totality thereof, for example as a complete continuous circular line. However, provision can also be made for the rhexis line to be determined in line sections and for these line sections to be displayed. As a result, there can be an optical segmentation of the rhexis line. In particular, provision can be made for the line sections at which the start of the actual rhexis is advantageously implemented to be displayed. Hence, even independently of the actual surgical intervention, a surgeon can advantageously be provided with an information item that communicates to them the best-possible starting point or start where the actual rhexis should begin. In such a segmentation of a rhexis line, it is likewise possible for a line segment or a line section of the rhexis line that follows the point of the rhexis start in the clockwise direction to then be optically displayed and/or for that line section or that line segment that follows or adjoins the point of the rhexis start in the anticlockwise direction to then be optically displayed. As a result of this, a possible situation-dependent information overload for a surgeon is prevented and only those line segments that represent the reference at the start of an actual rhexis are initially displayed.

Proceeding from such a representation of merely line segments, it is also possible for individual further segments to be presented subsequently in time in a manner following the already optically displayed line segments. This achieves an optically dynamic display that also offers the surgeon a dynamic impression of the advancing production of the potential actual rhexis. Even in the representation in a simulation of the dynamic rhexis formation over the entire tear line of the actual rhexis in this respect, this consequently optically represents an information item to the specialist medical staff, independently of the actual operation on the eye to be performed.

There can also be provision for those line segments of the optically displayed reference rhexis where the tear line of an actually present actual rhexis has already been produced over their length to be blocked out again. This also means that only those line segments over the length of which the tear line of the actual rhexis should still be produced are optically displayed or remain optically displayed in dynamic fashion during a surgical intervention. Consequently, the one optical information item that may then no longer be paramount is removed such that a surgeon is not distracted thereby.

In a further embodiment, provision is made not only for the reference rhexis to be determined and displayed during the production of this reference information item but also for, additionally, the handling of the mechanical tearing tool by the ophthalmic surgical apparatus to be determined and to be optically displayed on the display unit. In this context, provision can be made for the evaluation unit to determine individual orientations and pulling directions of the mechanical tearing tool, at least at certain critical points of the reference rhexis, and to display these on the optical display unit. Here, the mechanical tearing tool can be displayed as a real object on the optical display unit or it can be displayed by way of a symbol. By way of example, a symbolic representation can also be implemented as an arrow which, in particular, represents the pulling direction on the already lacerated flaps of the anterior capsular bag wall by way of the arrow direction. The display can also be implemented in dynamic fashion such that the direction of the arrow can change, for example depending on the previous tear direction and/or the expected tear direction and/or the previous orientation of the tearing tool and/or the previous pulling force on the anterior capsular bag wall by the tearing tool. Additionally, the shape and/or the color of the symbol, more particularly of the arrow, may emerge depending on the implemented treatment situations and/or treatment situations expected in future. Consequently, critical tear states that have occurred and/or critical tear states to be expected can also be visually and/or acoustically indicated to the surgeon and the latter can react thereto. In addition or as an alternative thereto, a flashing of the symbol, for example, can optically indicate such a critical tear state or a critical tear state to be expected. Consequently, the entire possible surgical procedure is possibly displayed to the surgeon in simulated fashion if desired, the entire possible surgical procedure having been determined, as it were, by the evaluation unit. Therefore, the theoretical procedure can be proposed to the surgeon, for example even already before a real or simulated surgical intervention on the eye. Then, in the context based on the reference rhexis that has been determined and optically displayed, the surgeon then knows how they must react at possibly critical points in an operation to be actually performed or the surgeon is already prepared for this in this context. Hence, the surgical intervention is improved since the surgeon is already prepared for possible difficulties during the actual surgical intervention as a result of this embodiment of the reference rhexis and the production of the opening, presented in advance in theoretical fashion and in simulation.

In this context, it is likewise also possible for such an information item about the temporal profile of the reference rhexis to be displayed on the optical display unit by a video. It is likewise possible for an assisting information item and/or auxiliary information item to be displayed on the optical display unit if a deviation of the actually present or actual rhexis from the reference rhexis occurs. This also allows aiding scenarios to be shown to and trained by a surgeon independently of a surgical intervention to then be actually performed, should deviations by the actually present rhexis then occur at specific points of the reference rhexis. This also allows the medical staff to be trained for specific situations independently of an intervention to be actually performed and this also allows individual aspects to be shown and learnt by simulation.

It is also possible for the medical staff to communicate with the ophthalmic surgical apparatus to the effect of specific situations being able to be queried. By way of example, provision can be made in this context for a surgeon to then undertake modifications if they receive a specific reference rhexis that was determined by the evaluation unit and displayed on the optical display unit. By way of example, a surgeon or any other medical staff member may mark specific points of this shape of the reference rhexis on the optical display unit, which generally may also be embodied as a touch-sensitive operating field, for example, or which has other selection means. In particular, it is also possible to be able to mark points or plot other lines, which represent a specific deviation from the curve of the reference rhexis, on this optical display unit. Hence, the evaluation unit can then also be provided with information to the effect of the evaluation unit proposing modes of action in respect of how the mechanical tearing tool, for example, should subsequently be handled if such a deviation from the optically displayed reference rhexis should occur during the actual surgical intervention. This also allows the surgeon or other specialist medical staff to imagine specific critical situations without an actual operation and, for example, also to train these.

In an embodiment, provision is made of an image of an eye, more particularly an image of an eye in which a rhexis should be performed on the anterior capsular bag wall, being produced by an image producing unit of the ophthalmic surgical apparatus. The determined reference rhexis is represented in this image as an optical superposition. As a result, a particularly realistic representation of the size and position of the determined reference rhexis is presentable on the eye provided to this end. This facilitates a particularly realistic representation. As a result, a surgeon obtains a particularly realistic representation of the overall situation.

Advantageously, the anterior capsular bag wall can be presented in this image and the reference rhexis is presented in superposed fashion at the position of the presented anterior capsular bag wall at which the actually present actual rhexis should be implemented in the anterior capsular bag wall during a surgical intervention. Hence, independently of the actual surgical intervention, the surgeon already obtains an overall impression as to how the actual rhexis will present itself on the capsular bag and whether this also actually corresponds to the surgeon's ideas and whether this can be produced accordingly. Depending on the type of intraocular lens that should be implanted in the capsular bag, the surgeon can then consequently already identify whether the opening in the anterior capsular bag wall produced by the reference rhexis is even actually suitable in terms of size and/or in respect of the position, independently of a surgical intervention.

Preferably, provision can be made for the movement of a mechanical tearing tool, which is used to lacerate the anterior capsular bag, to be captured during a surgical intervention by way of a capturing appliance of the ophthalmic surgical apparatus and/or for a previously performed tear line of the performed actual rhexis to be captured and/or for a future tear line of the actual rhexis to be determined. Depending on at least one of these intervention information items, a deviation that has already occurred of the actually present actual rhexis from the determined and optically displayed reference rhexis is determined and/or a deviation of the actually present actual rhexis from the determined and optically displayed reference rhexis that may occur in future is determined or estimated.

This is a further advantageous embodiment since this therefore also allows an already started surgical intervention to be corrected or interrupted and consequently it is possible, independently of a surgical intervention, to test the extent to which the previous operation result is desired or forms a suitable starting point for a subsequent continuation of the surgical intervention. However, provision can also be made for this advantageous embodiment to in fact also be carried out during the surgical intervention and consequently during the dynamic production of the actual rhexis in the anterior capsular bag wall by the mechanical tearing tool. Hence, as an accompaniment to the surgical intervention, it is also possible to constantly monitor, particularly in permanent and continuous fashion, whether the dynamic tear formation in the anterior capsular bag wall corresponds to the determined and optically displayed reference rhexis.

Consequently, this also allows the actual tear formation, and consequently also the actual rhexis, at the anterior capsular bag wall to be compared to the theoretically determined new rhexis, specifically the reference rhexis, during the surgical intervention. Secondly, it is also possible to interrupt the operation and carry out this analysis during the interruption. Then, only the result of the already completed surgical intervention is evaluated.

In an embodiment, provision is made for a warning message that is, for example, optically visible and hence visual or for an acoustic warning message to be produced in the case of a deviation that is greater than a tolerance value. Consequently, a surgeon is also educated or trained so as to be able to quickly identify what critical deviations could be and what reaction can be carried out. This is advantageous during a real surgical intervention then to be actually carried out since a surgeon has already themselves learnt, in particular by way of the training scenarios with the evaluation unit, to sense what critical deviations could be and how to be able to automatically react thereto where necessary.

In addition or as an alternative thereto, provision can be made for the color of the displayed reference rhexis to be changed in the case of a deviation that is greater than a tolerance value, at least in the length region in which the deviation has occurred or could occur. As a result, an optical display of this possibly undesired deviation is also imparted as an alternative or in addition to an acoustic warning message.

In addition or as an alternative thereto, provision can be made for the reference rhexis to be displayed in flashing fashion, at least in the length region in which the deviation has occurred or could occur. This also attracts attention to prevent or respond to unwanted states.

Preferably, provision can be made for a preferred movement of the tearing tool during further laceration to be determined in the case of a deviation that is greater than a tolerance value and optically displayed on the display unit.

In an embodiment, provision is made for, for example, a diameter of the area that is removed from the anterior capsular bag wall by the rhexis line to be entered as rhexis size as a characterization information item. In addition or as an alternative thereto, a reference site or a reference point at which the rhexis should be centered can be specified as a rhexis position. By way of example, a center of the rhexis embodied as a circular line may be specified here, the center being predetermined as centered with respect to a pupil of the eye, for example.

Provision is made in an embodiment for not only one image but for a plurality of images of the eye to be produced and provided and, in this respect, for the eye to be identifiable from different positions, in particular. This allows an even more accurate position of the reference rhexis to be presented and identified.

Advantageously, image recordings can be implemented and evaluated at certain times or continuously during an actually performed surgical intervention. As a result, it is possible to identify more accurate information items about a possible deviation between a reference rhexis and the actually present actual rhexis. By way of example, an intersection between an already lacerated capsular bag and an edge of the reference rhexis can be better identified here. In particular, the dynamic movement and/or position of a tearing tool can then also be identified and evaluated in improved fashion. The form of the respectively already formed actual rhexis can also then be identified in improved fashion, in particular on account of the different perspectives provided by the different images.

Preferably, provision can also be made for the ophthalmic surgical apparatus to include more than two capturing appliances, which are arranged at different positions and which facilitate the recording of the eye from different perspectives. Using this, it is also possible for the evaluation unit to evaluate an improved assessment of a future profile of the actual rhexis.

Advantageously, the reference rhexis can be displayed in two-dimensional or else three-dimensional fashion. In particular, an image of the eye on which then the reference rhexis is advantageously presented, particularly in superposed form, can also be two-dimensional and three-dimensional.

Since the real or natural capsular bag hangs around its circumferential edge on zonular fibers that have a certain elasticity, the eyeball with the capsular bag contained therein in each case moves in the direction in which force is exerted on the capsular bag by the mechanical tearing tool. Aligning the recorded images of the eye with respect to a reference of the eye, for example the pupil, is advantageous for the purposes of a more accurate evaluation. This allows this dynamic movement or the relative movement between individual parts of the eye to be evaluated. This in turn is advantageous for the determination of the actual rhexis and for the determination of the deviation of the actual rhexis from the reference rhexis.

In particular, these information items about relative movements and/or deformations of parts of the eye in the case of a mechanical action by the mechanical tearing tool also allow the determined and optically displayed reference rhexis to be adapted thereto. In particular, there is an adaptation, more particularly also dynamically displayed adaptation, of the reference rhexis on the basis of a change of form and/or the direction of the change in form caused at the capsular bag by the action of this force. In this context, the dynamically changed form of the reference rhexis can then be determined and likewise optically displayed.

Instead of the pupil, at least one blood vessel in the sclera, for example, may also be a further reference in respect of which the capsular bag can move during an intervention with the mechanical tearing tool.

In order to account for the virtually spherical form of the capsular bag in an improved fashion, it is also possible to also take account of the spatial position and movement of the actual tear and of the tip of the mechanical tearing tool, in particular by a three-dimensional recording, optical capturing system and consequently by a three-dimensionally produced image, in particular. As a result, the accuracy of the analysis, in particular of a possible deviation between the actual rhexis and the determined and optically displayed reference rhexis, can be satisfied.

An aspect of the invention relates to a method for producing a medical information item, an auxiliary information item, in particular a surgical auxiliary information item. The auxiliary information item is formed by at least one reference rhexis, as has been produced by the aforementioned method. In particular, the auxiliary information item is formed by the reference rhexis and, more particularly, at least one image on which the reference rhexis is superposed, more particularly superposed in locally precise fashion, at least in regions. The auxiliary information item can be a reference information item of the eye. At least a portion of the eye, more particularly an anterior capsular bag wall, is presented in the image, which may be a recorded image, for example recorded by an image producing unit, or a microscope image. At this point, at which an actual rhexis is intended to be produced in the capsular bag wall, the reference rhexis is presented in a manner superposed on this capsular bag wall in locally precise fashion. In particular, the actual rhexis should be produced along the reference rhexis displayed as a rhexis line. In particular, this auxiliary information item can be provided in a method for carrying out a surgical intervention on an eye, more particularly on a capsular bag of an eye, which relates to a further aspect of the invention. This auxiliary information item is optically displayed on the anterior capsular bag wall, in particular. The anterior capsular bag wall is lacerated by means of a mechanical tearing tool and the profile of the rhexis is produced taking account of the reference rhexis, more particularly produced to the best possible extent along the reference rhexis.

A further aspect of the invention relates to an ophthalmic surgical apparatus having an input unit, an evaluation unit and an optical display unit. The apparatus is embodied to carry out a method according to the aforementioned aspect or an advantageous embodiment thereof. In particular, this method is carried out by the apparatus.

The features and feature combinations mentioned in the description above and the features and feature combinations mentioned in the description of the figures below and/or only shown in the figures may be used not only in the respectively specified combination, but also in other combinations, without departing from the scope of the invention. Hence, embodiments of the invention which are not explicitly shown and explained in the figures but which emerge from the explained embodiments by way of separate feature combinations and which are producible should also be considered to be comprised and disclosed. Therefore, embodiments and feature combinations which do not have all the features of an originally phrased independent claim should also be considered to be disclosed. Furthermore, embodiments and feature combinations, in particular by virtue of the embodiments explained above, which go beyond or deviate from the feature combinations explained in the dependency references of the claims should be considered to be disclosed.

The concrete values indicated in the documents for parameters and indications concerning ratios of parameters or parameter values for the definition of embodiments of the apparatus should be considered to be concomitantly encompassed by the scope of the invention even in the context of deviations, for example on account of measurement errors, system faults, DIN tolerances, et cetera, which means that explanations relating to substantially corresponding values and indications should also be understood thereby.

BRIEF DESCRIPTION OF THE DRAWINGS

The invention will now be described with reference to the drawings wherein:

FIG. 2 shows a simplified illustration of an image in a plan view of an eye and a reference rhexis optically superposed on the eye; and, FIGS. 3A to 3E show respective plan views of an eye in different states of an anterior capsular bag wall before and during the performance of a rhexis.

DESCRIPTION OF THE PREFERRED EMBODIMENTS OF THE INVENTION

Figure 1:
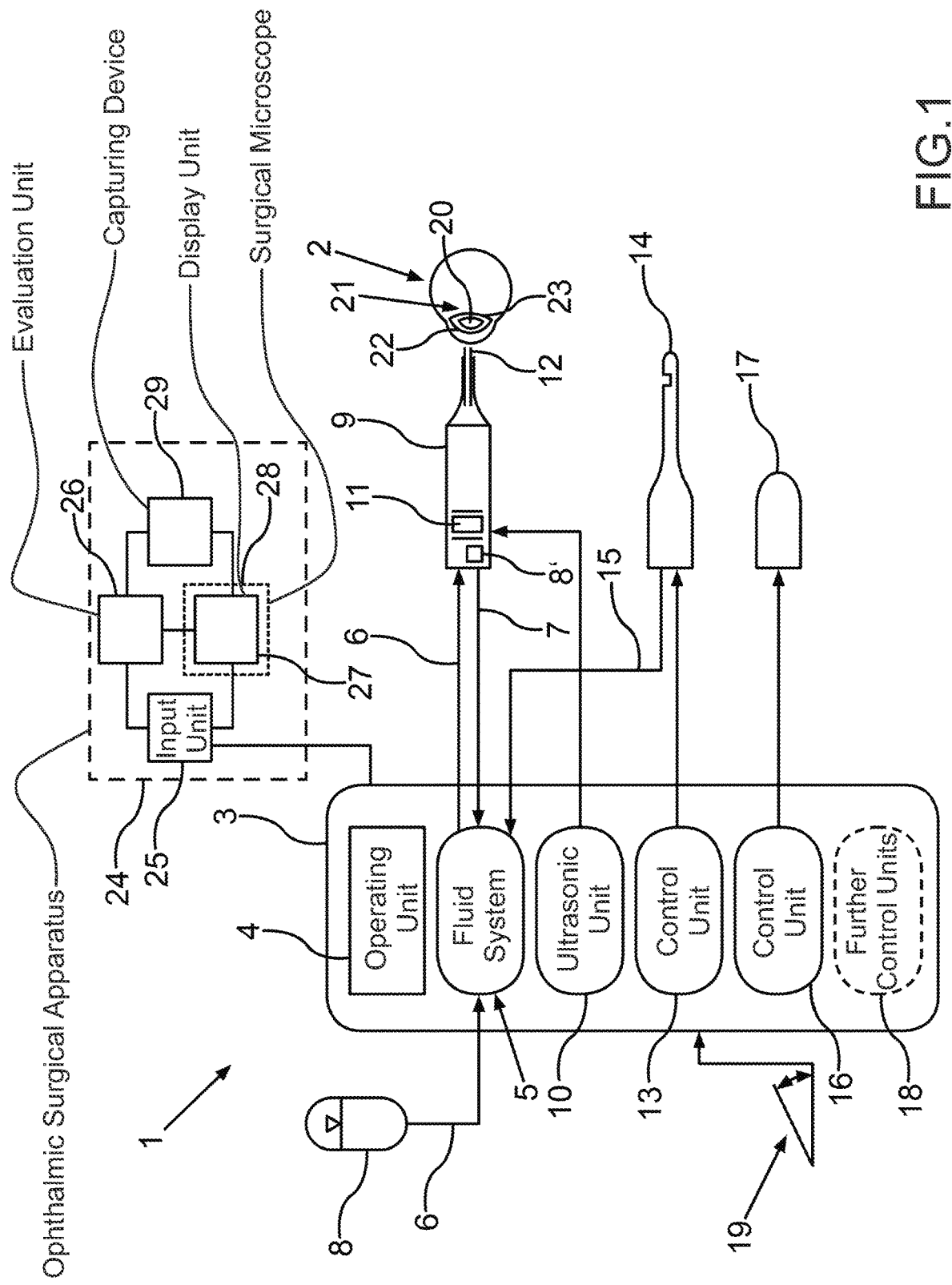
FIG. 1 shows a schematic illustration of an ophthalmic surgical system including an embodiment of an ophthalmic surgical apparatus.

In the figures, identical or functionally equivalent elements are provided with the same reference signs.

FIG. 1 shows a schematic illustration of an ophthalmic microsurgical system or an ophthalmic surgical system 1 for phaco-surgery on an eye 2. The illustration according to FIG. 1 shows a few of the components of the system 1 in symbolic fashion for a simplified explanation of the basic general functionality of the system 1.

The system 1 includes a device unit 3, which can be, for example, a trolley or the like. Preferably, an operating unit 4 can be arranged in or on the device unit 3. By way of example, this operating unit 4 may include a user interface, an input unit such as a keyboard or the like and a display unit such as a monitor or display. Furthermore, a fluidic system 5 that includes a pump and a control unit for controlling the pump and connected components can preferably be arranged in the device unit 3. The fluidic system 5 includes an irrigation apparatus 6 with an irrigation branch and an aspiration apparatus 7 with an aspiration branch. The irrigation apparatus 6 includes a container 8 for rinsing liquid, for example a BSS solution, which is an irrigation fluid which is guided to a phaco-handpiece. The phaco-handpiece is an ophthalmic surgical handpiece 9. In particular, it is a constituent part of the ophthalmic surgical system 1. The aspiration apparatus 7 is likewise connected to the ophthalmic surgical handpiece 9. Moreover, the device unit 3 includes an ultrasonic unit 10 in particular, the latter being embodied to excite an oscillation of a piezo-component 11 in the ophthalmic surgical handpiece 9, by means of which a hollow needle 12 of the ophthalmic surgical handpiece 9 is excited to oscillate. Further, the device unit 3 includes a control unit 13, in particular. The control unit 13 can also be embodied to control a vitrectomy handpiece 14, which, in particular, may be a constituent part of the ophthalmic surgical system 1. Preferably, the vitrectomy handpiece 14 may also be connected to the fluidic system 5, in particular by an aspiration line 15. Moreover, provision can be made for a further control unit 16, the latter controlling a preferably available further surgical instrument 17, for example for diathermy. Moreover, the system 1 and, more particularly, the device unit 3 may include further modules and control units and systems, which are represented symbolically by the unit 18. This also includes further internal units, and also peripheral devices. Moreover, the ophthalmic surgical system 1 may preferably include a foot control panel 19, which is connected to the device unit 3, more particularly to communication appliances and control units of the device unit 3.

The eye 2 can be a real, living eye. It includes a natural lens 20, which is arranged in a capsular bag 21. The capsular bag 21 includes an anterior capsular bag wall 22 and a posterior capsular bag wall 23. The eye 2 can be a real eye of a human or an animal. However, it can also be a dummy eye. In this embodiment, it may have been taken from a dead organism and be a dummy eye made of biological material. However, the dummy eye may also be manufactured artificially, for example, and be formed at least in part from plastics, for example. However, it may also be an eye that is only presented on a screen in a simulation. In this embodiment, the eye 2 can be presented in 2 dimensions or 3 dimensions. The dummy eyes or the eye produced by simulation also include(s) the usual components, in particular a lens 20 and a capsular bag 21.

FIG. 1 shows an embodiment of an ophthalmic surgical apparatus 24. The ophthalmic surgical apparatus 24 can be a constituent part of the ophthalmic surgical system 1. However, the ophthalmic surgical apparatus 24 can also be a separate apparatus. It can likewise be used in the actual real surgical intervention on a real eye 2; however, by way of example, it can also be used for training purposes or education purposes for medical staff. The apparatus 24 can also be used as a separate unit without the system 1, particularly for training or education purposes.

The ophthalmic surgical apparatus 24 includes at least one input unit 25. The latter can be a keyboard. However, it can also be a touch-sensitive input field. However, in addition or as an alternative thereto, the input unit 25 can also be embodied for speech input.

The ophthalmic surgical apparatus 24 preferably may include an evaluation unit 26. In particular, the evaluation unit 26 is also embodied to evaluate the input information items that are input via the input unit 25. The ophthalmic surgical apparatus 24 preferably may include an optical display unit 27. This optical display unit 27 can be a separate screen. However, the optical display unit 27 can also be a constituent part of a surgical microscope 28, for example.

The ophthalmic surgical apparatus 24 may preferably include at least one capturing appliance 29. By way of example, the capturing appliance 29 can be an image producing unit such as a camera. In particular, this image producing unit is sensitive in the spectral range that is visible to humans.

In addition to the aforementioned use purposes, the apparatus 24 can also be embodied purely as an analysis apparatus. In such a configuration, theoretically simulated trials or conceptual approaches of a medical staff member can be tested and analyzed for the purposes of producing a best-possible rhexis. In addition to this embodiment as a trial apparatus, the apparatus 24 can also be used as an analysis apparatus. In such a configuration, operation results of an already completed real operation can also subsequently be evaluated and analyzed.

Using the ophthalmic surgical apparatus 24, it is possible to carry out a method for producing a reference information item of an eye. In particular, this method is carried out by the ophthalmic surgical apparatus 24. Moreover, the ophthalmic surgical apparatus 24 is embodied to provide this produced reference information item of an eye. In particular, what is allowed in this case is that this reference information item is also provided during a real operation and consequently during a real surgical intervention on the eye 2. At least one characterization information item is input into the input unit 25 for the purposes of producing the at least one reference information item of an eye. By way of example, an input can be implemented manually by a medical staff member, more particularly a surgeon. In this context, specific values of the characterization information item can be input into the input unit 25. An input can also be implemented to the effect of values of at least one characterization information item that are stored in the input unit 25 being offered in the input unit 25 and a desired value then being selected by the medical staff, for example.

In particular, a rhexis size and/or rhexis position of a potential rhexis are/is input into the input unit 25 as a characterization information item. By way of example, a shape of the rhexis and a geometric parameter, such as a radius or a diameter, for example, can be input as a rhexis size. The position of the potential actual rhexis with respect to a reference point in the eye can be input as a rhexis position. In particular, an information item in respect of which the actual rhexis should be centered can be input as a rhexis position in this context. By way of example, a center of the geometry of the potential actual rhexis can be input, more particularly in relation to another component of the eye such as a pupil and/or a blood vessel of the sclera, for example.

A theoretical reference rhexis is determined as a reference information item of the eye by the evaluation unit 26, depending on this at least one characterization information item. This determined reference rhexis is displayed in optically perceivable fashion by the optical display unit 27.

Preferably, provision can be made for a two-dimensional or three-dimensional image of the eye to be recorded by the at least one capturing appliance 29, it being possible for the eye to be an artificial dummy eye or a real dummy eye, for example taken from a dead organism, or a real eye 2. Provision can be made for a plurality of capturing appliances 29 to be provided, by means of which at least one image of this eye is captured in each case such that a plurality of images from different perspectives can be present for the respective eye.

In particular, the determined reference rhexis is also presented optically on the image as a superposition, in particular presented superposed with respect to the anterior capsular bag wall 22 presented in the image. In particular, a rhexis line is produced and optically displayed as a reference rhexis. Preferably, this rhexis line can be a continuous line, more particularly a circular line.

In this context, FIG. 2 shows a schematic illustration of an image 30. At least a portion of an eye, for example of the eye 2, is presented in the image 30. In particular, the capsular bag 21 with the anterior capsular bag wall 22 is shown in this case. Zonular fibers 31 are likewise represented in symbolic fashion. Moreover, it is possible to identify the lens 20. A complete reference rhexis 32 is optically displayed as a rhexis line and presented in a manner superposed on the anterior capsular bag wall 22. This image 30 can be presented on an external screen or in an eyepiece of a surgical microscope 28.

FIG. 3A shows a capsular bag 21 of an eye, for example of the real eye 2, in a schematic and simplified illustration.

For the purposes of removing the lens 20 from the capsular bag 21, the anterior capsular bag wall 22 is contacted and lacerated using a mechanical tearing tool 33, particularly in the case of a real surgical intervention on the real eye 2, as shown in FIG. 3B. This tearing tool 33 can be a needle or forceps. In particular, in this context, this tearing tool 33 is introduced as far as the capsular bag 21 through an incision in the cornea and the actual rhexis is produced there by direct contacting and lacerating of the anterior capsular bag wall 22. The actual rhexis is the region of the anterior capsular bag wall 22 that is lacerated. It is delimited by a tear line. In particular, provision is made here for the reference rhexis 32 to be presented optically as a superposition before the start of the actually present actual rhexis using the tearing tool 33. Consequently, as already explained with respect to FIG. 2, this reference rhexis 32 is presented in the image 30 in a precise position in a manner perceivable for the medical staff. In particular, this reference rhexis 32 predetermines by way of an optical presentation that tear line that should in fact be produced in the anterior capsular bag wall 22 when carrying out the actual rhexis. If this actual rhexis is implemented in the region of this reference rhexis 32, more particularly as congruent thereto as possible, as illustrated in FIG. 3C, the opening 34, determined and defined in advance, in the anterior capsular bag wall 22 is produced. Then, the lens 20, in particular in the comminuted state, can be removed through this opening 34 and an intraocular lens can be implanted in the capsular bag 21. In particular, the tear line of the actual rhexis should be implemented along the reference line of the reference rhexis 32. In FIG. 3B, the hatched region 36 represents that portion of the entire opening 34 that has already been produced and over which the lacerated anterior capsular bag wall 22 has been pulled away by the tearing tool 33. The interior of the capsular bag 21, and consequently the lens 20, has already been exposed in the hatched region 36. This also applies in the further FIGS. 3C to 3E, with FIG. 3C illustrating the completely produced opening 34.

In contrast to FIG. 3B, the illustration in FIG. 3D shows a situation in which the actual rhexis 35 deviates from the reference rhexis 32, in particular deviates to the effect of having torn towards a circumferential edge of the capsular bag 21 and towards the zonular fibers 31. Such an embodiment is unwanted and can be avoided by the production and optical presentation of the reference rhexis 32. Consequently, the aforementioned method can avoid a situation in which a tear reaches close to the circumferential edge of the capsular bag 21, as shown in FIG. 3D, since such incorrect tears are recognized in good time and are avoided.

On the other hand, as illustrated in FIG. 3E, if only a small deviation has occurred between the optically displayed reference rhexis 32 and the actually present actual rhexis 35, this can be monitored and identified by the ophthalmic surgical apparatus 24. If this deviation is greater than a threshold, it is possible, for example, for an acoustic and/or visual message to be output to the medically responsible person and/or for the color of the indicated reference rhexis 32, in particular in the current length section of the reference rhexis embodied as a line, to be changed and/or for the reference rhexis 32 to be presented in flashing fashion, at least in the length section in which the deviation has occurred. This may also be determined for a length section of the actual rhexis 35 yet to occur in future and, accordingly, the reference rhexis 32 can then likewise be changed in terms of its color in a further length section and/or, for example, be presented in flashing fashion. Therefore, an anticipatory optical information item can also be provided for medical staff, this optical information item relating to how the actual rhexis 35 will be presented in future if the tearing tool 33 is used on the basis of the current orientation and/or movement and/or movement direction on the anterior capsular bag wall 22, for example, and/or this anticipatory evaluation can be implemented on the basis of the previous profile of the actual rhexis 35.

In addition to the reference rhexis 32, the display unit 27 can also display an information item, in particular also in optical and symbolic fashion, for example also by way of an avatar, the information item indicating how the tearing tool 33 should be oriented and/or held during the further production of the actual rhexis 35 and/or the direction in which the tearing tool should be moved in order to lie as close as possible to the reference rhexis 32.

Provision can be made for a capture of the eye 2 by the at least one capturing appliance 29 to be carried out continuously during the production of the actual rhexis 35 and for the corresponding image information items to be evaluated by way of the evaluation unit 26. As a result, information items about the direction and speed of the already implemented cut or of the actual rhexis 35, and also the then-expected future orientation or curve of the actual rhexis 35, can be determined also on the basis of different perspectives in these images. By way of example, this can be implemented on the basis of the intersection of a tear line of an already torn part of the anterior capsular bag wall 22 and an edge of the reference rhexis 32. This can also be implemented on the basis of the position and/or orientation and/or movement direction of the tearing tool 33. It is likewise possible for this determination to be implemented on the basis of a line of extent of the previously formed actual rhexis 35 and/or on the basis of the area and form of the surface region of the potential entire opening 34 that has already been exposed by the previously implemented actual rhexis 35.

Since the capsular bag 21 hangs around the circumference edge on the aforementioned zonular fibers 31 and suspended there with a certain elasticity, the eyeball with the capsular bag 21 contained therein respectively moves in the direction in which force is exerted. In order to improve the evaluation, it is possible for the images produced by the at least one capturing appliance 29 to be aligned with respect to at least one reference component in the eye 2, such as, for example, the pupil and/or the iris and/or at least one blood vessel in the sclera. In order to satisfy the substantially spherical form of the capsular bag 21, in particular, it is also possible that a three-dimensional imaging system, in particular, is formed by the capturing appliance 29. As a result, the spatial position and the movement or the continuously produced profile of the actual rhexis 35 and, in this context, the movement of the tip of the tearing tool 33 can also be taken into account. As a result, the accuracy can be improved.

It is understood that the foregoing description is that of the preferred embodiments of the invention and that various changes and modifications may be made thereto without departing from the spirit and scope of the invention as defined in the appended claims.

What is claimed is:

1. A method for generating a reference information item of an eye with the aid of an ophthalmic surgical system for phaco-surgery on the eye, said ophthalmic surgical system including an input unit, an evaluation unit connected to said input unit, an optical display unit connected to said evaluation unit and a capturing device connected between said evaluation unit and said optical display unit, the method comprising:

inputting at least one characterization information item characterizing at least one of a rhexis size and a rhexis position of a potential and desired actual rhexis on an anterior capsular bag wall of the eye into said input unit of an ophthalmic surgical apparatus;

passing the characterization information item to said evaluation unit and determining therein, in dependence upon the characterization information item, a fictitious reference rhexis as at least a constituent part of the reference information item of the eye independently of an actual surgical intervention to be subsequently performed;

optically displaying the determined fictitious reference rhexis via said optical display unit of said ophthalmic surgical apparatus;

capturing via said capturing device, as an intervention information item or items, at least one of a movement of a mechanical tearing tool that is used to lacerate the anterior capsular bag wall and a previously produced tear line of a performed actual rhexis and/or determining a tear line of a rhexis that may occur in the future; and, determining, depending on at least one of said intervention information items, at least one of a deviation of the actual rhexis from the determined and optically displayed fictitious reference rhexis that has already occurred and a deviation of the actual rhexis from the determined and optically displayed fictitious reference rhexis that may occur in the future.

2. The method of claim 1, wherein the reference rhexis is optically displayed in an eyepiece of a surgical microscope of the ophthalmic surgical apparatus.

3. The method of claim 1, wherein the reference rhexis is optically displayed on a screen of the ophthalmic surgical apparatus.

4. The method of claim 1, wherein at least one rhexis line is optically displayed as the reference rhexis.

5. The method of claim 1, wherein at least one continuous rhexis line is optically displayed as the reference rhexis.

6. The method of claim 1, wherein at least one circular rhexis line is optically displayed as the reference rhexis.

7. The method of claim 1 further comprising capturing at least one image of the eye via a capturing apparatus of the ophthalmic surgical apparatus, wherein the reference rhexis is presented as an optical superposition on the image.

8. The method of claim 7, wherein at least the anterior capsular bag wall is represented in the image and the reference rhexis is represented in superposed fashion at a location of the represented anterior capsular bag wall at which an actual rhexis is implemented in the natural anterior capsular bag wall in a surgical intervention on the eye.

9. A method for generating a reference information item of an eye with the aid of an ophthalmic surgical system for phaco-surgery on the eye, said ophthalmic surgical system including an input unit, an evaluation unit connected to said input unit, an optical display unit connected to said evaluation unit and a capturing device connected between said evaluation unit and said optical display unit, the method comprising:

inputting at least one characterization information item characterizing at least one of a rhexis size and a rhexis position of a potential actual rhexis on an anterior capsular bag wall of the eye into said input unit of an ophthalmic surgical apparatus;

passing the characterization information item to said evaluation unit and determining therein, in dependence upon the characterization information item, a reference rhexis as at least a constituent part of the reference information item of the eye;

optically displaying the determined reference rhexis via said optical display unit of said ophthalmic surgical apparatus;

capturing via said capturing device, as an intervention information item or items, at least one of a movement of a mechanical tearing tool that is used to lacerate the anterior capsular bag wall and a previously produced tear line of a performed actual rhexis and/or determining a tear line of a rhexis that may occur in the future;

determining, depending on at least one of said intervention information items, at least one of a deviation of the actual rhexis from the determined and optically displayed reference rhexis that has already occurred and a deviation of the actual rhexis from the determined and optically displayed reference rhexis that may occur in the future;

further comprising at least one of:

generating a warning message when a deviation is greater than a tolerance value;

changing a color of the displayed reference rhexis at least in a length region in which the deviation has occurred or could occur; and, presenting the reference rhexis in a flashing fashion at least in the length region in which the deviation has occurred or could occur.

10. A method for generating a reference information item of an eye with the aid of an ophthalmic surgical system for phaco-surgery on the eye, said ophthalmic surgical system including an input unit, an evaluation unit connected to said input unit, an optical display unit connected to said evaluation unit and a capturing device connected between said evaluation unit and said optical display unit, the method comprising:

inputting at least one characterization information item characterizing at least one of a rhexis size and a rhexis position of a potential actual rhexis on an anterior capsular bag wall of the eye into said input unit of an ophthalmic surgical apparatus;

passing the characterization information item to said evaluation unit and determining therein, in dependence upon the characterization information item, a reference rhexis as at least a constituent part of the reference information item of the eye;

optically displaying the determined reference rhexis via said optical display unit of said ophthalmic surgical apparatus;

capturing via said capturing device, as an intervention information item or items, at least one of a movement of a mechanical tearing tool that is used to lacerate the anterior capsular bag wall and a previously produced tear line of a performed actual rhexis and/or determining a tear line of a rhexis that may occur in the future;

determining, depending on at least one of said intervention information items, at least one of a deviation of the actual rhexis from the determined and optically displayed reference rhexis that has already occurred and a deviation of the actual rhexis from the determined and optically displayed reference rhexis that may occur in the future;

further comprising:

determining a preferred movement of the mechanical tearing tool during a further laceration in the case of a deviation greater than a tolerance value; and, optically displaying the preferred movement on the display unit.

11. The method of claim 9 further comprising:
   determining a preferred movement of the mechanical tearing tool during a further laceration in the case of a deviation greater than a tolerance value; and,
   optically displaying the preferred movement on the display unit.

12. An ophthalmic surgical system for phaco-surgery on the eye, said ophthalmic surgical system comprising:
   an input unit configured for inputting at least one characterization information item characterizing at least one of a rhexis size and a rhexis position of a potential and desired actual rhexis on an anterior capsular bag wall of the eye;
   an evaluation unit connected to said input unit for receiving said characterization information item and being configured to determine, in dependence upon the characterization information item, a fictitious reference rhexis as at least a constituent part of a reference information item of the eye independently of an actual surgical intervention to be subsequently performed;
   an optical display connected to said evaluation unit and being configured to optically display the determined fictitious reference rhexis via an optical display unit of the ophthalmic surgical apparatus; and,
   a capturing device connected between said evaluation unit and said optical display and being configured to capture, as an intervention information item, at least one of a movement of a mechanical tearing tool that is used to lacerate an anterior capsular bag wall and a previously produced tear line of a performed actual rhexis and/or determining a tear line that may occur in the future; and,
   said evaluation unit being further configured to determine, depending on at least one of said intervention information items, at least one of a deviation of the actual rhexis from the determined and optically displayed fictitious reference rhexis that has already occurred and a deviation of the actual rhexis from the determined and optically displayed fictitious reference rhexis that may occur in the future.

\* \* \* \* \*